United States Patent [19]

Jansen et al.

[11] Patent Number: 4,591,729

[45] Date of Patent: May 27, 1986

[54] CONTROL UNIT FOR SWITCHING ON A TEACHING DEVICE

[75] Inventors: Hansjurgen Jansen; Karl-Heinz Gelsen, both of Pinneberg, Fed. Rep. of Germany

[73] Assignee: Sita Bauelemente GmbH, Pinneberg, Fed. Rep. of Germany

[21] Appl. No.: 624,588

[22] Filed: Jun. 26, 1984

[51] Int. Cl.⁴ .................................... H01H 35/00
[52] U.S. Cl. .............................. 307/116; 128/905; 434/308
[58] Field of Search ............... 307/116, 117, 140, 265, 307/518; 340/575; 128/722, 672, 732, 905; 434/308, 319; 377/20

[56] References Cited

U.S. PATENT DOCUMENTS

| | | | |
|---|---|---|---|
| 3,870,962 | 3/1975 | D'Errico | 307/265 X |
| 4,035,930 | 7/1977 | Lambert | 434/319 |
| 4,334,545 | 6/1982 | Shiga | 128/732 |
| 4,354,505 | 10/1982 | Shiga | 128/905 X |

FOREIGN PATENT DOCUMENTS

| | | | |
|---|---|---|---|
| 2840555 | 3/1980 | Fed. Rep. of Germany | 377/20 |
| 997074 | 2/1983 | U.S.S.R. | 434/308 |

Primary Examiner—A. D. Pellinen
Assistant Examiner—Derek S. Jennings
Attorney, Agent, or Firm—Collard, Roe & Galgano

[57] ABSTRACT

The control unit for switching on a teaching device for conveying optical and/or acoustical learning information which includes a transducer for converting the pulse, skin resistance, blood pressure or respiration as to intensity and rhythm into an electrical analog signal followed by a detector for delivering an electrical digital signal when the alpha-state of the test subject is reached. The detector controls a switching unit for switching on the teaching device when the digital signal is applied. The analog signal is additionally applied to a signal generator which feeds an output signal corresponding to the analog signal to a lamp and/or a loudspeaker for purposes of biofeedback.

3 Claims, 2 Drawing Figures

CONTROL UNIT FOR SWITCHING ON A TEACHING DEVICE

BACKGROUND OF THE INVENTION

1. Field of the Invention

The present invention relates to a control unit for switching on a teaching device and, more particularly, it relates to such a control unit which operates to switch on a teaching device when the test subject is in that state where learning ability is at its optimum.

2. Description of Prior Art

Teaching devices which convey learning information optically and/or acoustically are well known. However, it is also known that the test subject does not always possess the internal readiness and ability to absorb and permanently store information. In particular, sufficient learning ability is not always assured when the test subject is in the pure waking state, otherwise known as the beta-state. On the other hand, a test subject that is in the waking-somnolent state, otherwise known as the alpha-state, has a learning ability which is considerably greater than that in the beta-state.

SUMMARY OF THE INVENTION

It is, therefore, an object of the present invention to provide a control unit which switches on the teaching device being utilized when the test subject is in the alpha-state.

The control unit of the present invention makes use of the fact that better learning ability and perception exist in the alpha-state. The alpha-state itself can be ascertained for the test subject by pulse frequency, EEG or by respiration frequency, which drops in this state to an average of seven breaths per minute.

In order to facilitate the test subject entering into the alpha-state, the analog signal of the respiration frequency is indicated to him or her acoustically and/or optically, whereby a biofeedback effect is achieved, resulting in the test subject entering the alpha-state more easily and reliably. It is a particular advantage that it is possible to leave the acoustical and/or optical indication of the analog signal of the switched-on state of the teaching device connected parallel thereto, while the latter thus is conveying learning information.

The control unit of the present invention comprises a transducer which converts the pulse, skin resistance, blood pressure or respiration as to intensity and rhythm into an electrical analog signal which is fed to a detector which determines whether the alpha-state has been reached. The detector delivers a digital output signal to a switching unit which turns on the teaching device and at the same time the analog signal can be fed to a signal generator which feeds an output signal according to the analog signal to a lamp and/or a loudspeaker.

Other objects and features of the present invention will become apparent from the following detailed description considered in connection with the accompanying drawing. It is to be understood, however, that the drawing is designed as an illustration only and not as a definition of the limits of the invention.

BRIEF DESCRIPTION OF THE DRAWINGS

In the drawing wherein similar reference characters denote similar elements throughout the several views.

DESCRIPTION OF THE PREFERRED EMBODIMENT

Figure 1:
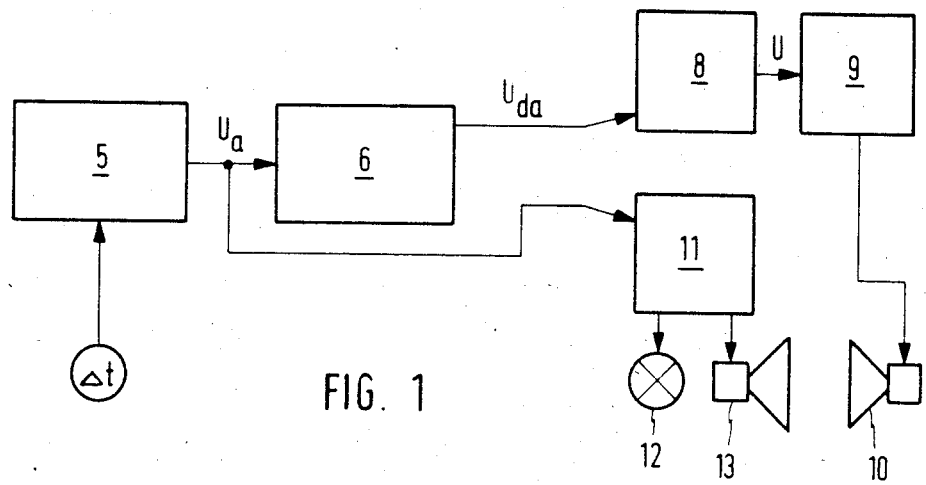
FIG. 1 is a schematic block diagram for the control unit according to the present invention.

Now turning to the drawing, there is shown in FIG. 1 a transducer, designated 5, which converts the respiration frequency of a test subject into a corresponding electrical analog output signal $U_a$. The transducer measures the temperature of the breath and, during exhalation, is enveloped by the spent air at body temperature. During inhalation, on the other hand, the transducer is enveloped by air at room temperature. The analog signal $U_a$ varies with the rhythm and intensity of respiration and is fed to a detector 6 which determines whether the alpha-state has been reached. In this case, detector 6 delivers a digital output signal $U_{da}$ to a switching unit 8 which in turn switches on the teaching device 9 proper, for instance via a loudspeaker 10 for the optical and/or acoustical conveyance of learning information.

At the same time, analog signal $U_a$ can be fed to a signal generator 11 which addresses in its rhythm a lamp 12 and/or loudspeaker 13. This optical and/or acoustical signal is directed to the test subject for the purpose of a biofeedback effect so as to induce the test subject to enter the alpha-state more easily.

Figure 2:
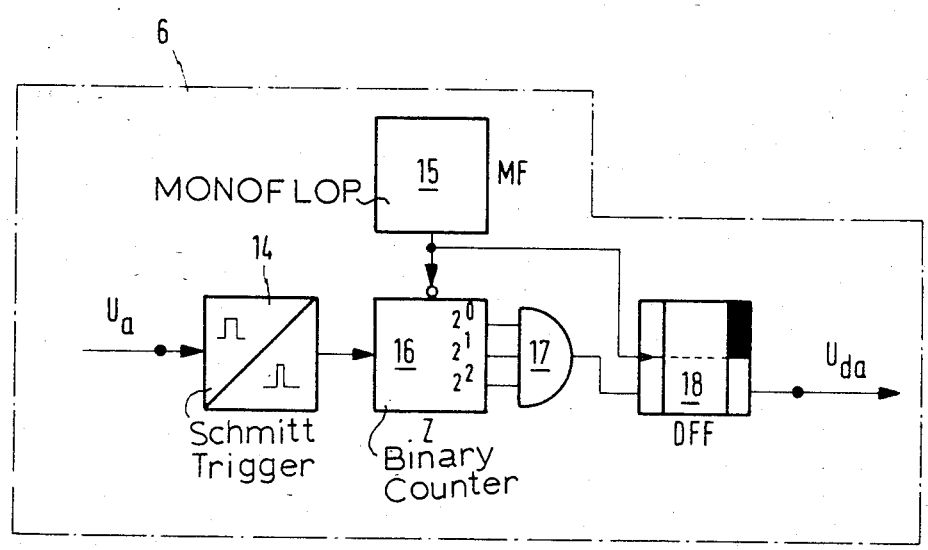
FIG. 2 is a schematic design of a portion of the control unit of FIG. 1.

FIG. 2 shows schematically the design of detector 6 of FIG. 1. The analog signal $U_a$ is fed to a Schmitt trigger 14 which converts the analog signal into digital pulses. These pulses are fed to a binary counter 16. The outputs of the counter are connected to each other via an AND gate 17. The output of the AND gate 17 is connected to the D-input of the D-flipflop 18, the output signal of which corresponds to the digital signal $U_{da}$.

Also provided is a monoflop 15, the output of which is connected to the asynchronous reset input of the counter 16 and to the clock input of the D-flipflop 18. The monoflop 15 delivers periodically a pulse once a minute. With this pulse, the value present at the D-input of the D-flipflop 18 is transferred into the flipflop and at the same time, the counter 16 is recessed for a new counting cycle. If the latter counts in the course of one minute seven pulses due to the respiration frequency of the test person who is in the alpha-state, each of its outputs ($2^0$, $2^1$ and $2^2$) carried a logical One. Only in this case, does the AND gate deliver an output signal in the form of a logical One, so that the output signal of the D-flipflop corresponds to the digital signal and always carries a logical One if the alpha-state has been reached.

While only a single embodiment of the present invention has been shown and described, it will be obvious that many changes and modifications may be made thereto without departing from the spirit and scope of the present invention.

What is claimed is:

1. A control unit to switch on a teaching device which conveys optical and/or acoustical information when the alpha-state of a test subject is reached as determined by the pulse, skin resistance, blood pressure or respiration of the test subject, said control unit comprising:
   a transducer which converts the pulse, skin resistance, blood pressure or respiration of the test subject as to intensity and rhythm into an electrical analog signal;
   a detector connected to said signal to deliver an electrical digital signal when the alpha-state is reached;

a switching unit connected to said detector to switch on the teaching device when the digital signal is applied; and a signal generator to which the analog signal of said transducer is fed, said signal generator feeding an output signal according to the analog signal to a lamp and a loudspeaker for biofeedback effect.

2. The control unit as defined in claim 1, wherein said detector comprises a Schmitt trigger converting the analog signal into digital pulses, a counter for the digital pulses having outputs and a reset input, a gate for the outputs of the counter for determining the counter reading, a D-flipflop the input of which is connected to the output of said gate, the output of said D-flipflop carrying the digital signal and said D-flipflop having a clock input, and a periodically triggered monoflop the output of which is connected to the reset input of the counter as well as to the clock input of the D-flipflop.

3. The control unit as defined in claim 2, wherein the counter is a binary counter, the gate is an AND gate and the monoflop has a pulse repetition frequency of one minute.

* * * * *